Figure 1:
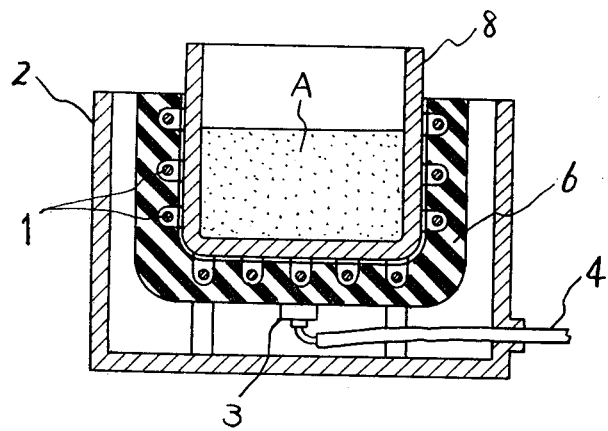

United States Patent [19]

Nishimura et al.

[11] 4,163,038
[45] Jul. 31, 1979

[54] FUMIGATING METHOD AND APPARATUS

[75] Inventors: Akira Nishimura; Takanobu Kashihara; Fukuyasu Okuda; Masanaga Yamaguchi, all of Ako, Japan

[73] Assignee: Earth Chemical Company, Limited, Hyogo, Japan

[21] Appl. No.: 882,921

[22] Filed: Mar. 2, 1978

[30] Foreign Application Priority Data

Mar. 3, 1977 [JP] Japan .................................. 52/23475
Apr. 20, 1977 [JP] Japan .................................. 52/45585
May 13, 1977 [JP] Japan .............................. 52/61975[U]

[51] Int. Cl.² .......................... A61L 1/00; A61L 3/00; A01M 13/00
[52] U.S. Cl. ........................................ 422/36; 43/125; 43/129; 71/DIG. 1; 252/350; 422/1; 422/28; 422/37; 422/305; 424/40
[58] Field of Search ..................... 21/117, 119, 108; 43/125, 129; 252/350; 424/40, 41, 42; 422/28, 29, 30, 31, 32, 33, 34, 35, 36, 37, 39, 125, 305, 1; 71/DIG. 1

[56] References Cited

U.S. PATENT DOCUMENTS

| | | | |
|---|---|---|---|
| 586,759 | 7/1897 | Cock | 21/117 |
| 1,652,291 | 12/1927 | Tanner | 21/108 UX |
| 2,071,171 | 2/1937 | McConnell | 424/42 X |
| 2,440,082 | 4/1948 | Flanders et al. | 21/108 UX |
| 2,497,612 | 2/1950 | Katzman | 21/117 |
| 2,540,095 | 2/1951 | Buehler | 21/119 UX |
| 2,590,529 | 3/1952 | Gillies et al. | 21/108 UX |
| 2,682,461 | 6/1954 | Hutchison | 424/40 X |
| 2,690,501 | 9/1954 | Laibow | 21/119 X |
| 2,767,511 | 10/1956 | Kissner et al. | 21/119 X |
| 2,813,187 | 11/1957 | Riba Rovira | 21/119 X |
| 3,446,893 | 5/1969 | Hanford et al. | 252/350 X |
| 3,645,931 | 2/1972 | Normanton et al. | 252/350 X |
| 3,903,015 | 9/1975 | Roos et al. | 252/350 |
| 3,956,849 | 5/1976 | Radulescu | 424/42 X |

FOREIGN PATENT DOCUMENTS

| | | | |
|---|---|---|---|
| 46-19080 | 5/1971 | Japan | 21/108 |
| 50-125039 | 10/1975 | Japan | 21/108 |
| 673429 | 6/1952 | United Kingdom | 21/119 |
| 699766 | 11/1953 | United Kingdom | 21/117 |

*Primary Examiner*—Barry S. Richman
*Attorney, Agent, or Firm*—Armstrong, Nikaido, Marmelstein & Kubovcik

[57] ABSTRACT

A mixture of an active ingredient and a blowing agent is heated indirectly with a heating element to thermally decompose the blowing agent and to volatilize the active ingredient. The mixture and the heating element are separated from each other by a partition which provides a heat transfer surface.

16 Claims, 7 Drawing Figures

FUMIGATING METHOD AND APPARATUS

This invention relates to a method of fumigating the interior of rooms and other confined spaces for controlling vermin and for fungicidal and incensing purposes, and an apparatus therefor, and more particularly to fumigating method and apparatus which are capable of concentrically producing such effects within a short period of time e.g. a few minutes or ten-odd minutes. The present method and apparatus are especially useful for controlling noxious insects, such as mosquitoes, flies and cockroaches, which are detrimental to man and also other insects, such as plant lice, green house whiteflies and caterpillars, which are harmful to agricultural plants.

As a method of controlling noxious insects, fumigation is known in which compositions of an active chemical and a combustible material are used, such that the combustible material, when burned, gives off heat and smoke, the heat causing the active ingredient to concentrically vaporize within a short time and the smoke assisting the volatilization of the ingredient. In order to quickly volatilize a great amount of active ingredient, the combustible materials useful for fumigating compositions are those capable of evolving a large quantity of smoke. The large quantity of smoke emitted by such combustible material generally has a pungent odor and high toxicity, is harmful to the human body and might possibly be mistaken for a fire. Soot and the like contained in the smoke tend to soil household furniture and walls in rooms. The combustible material involves a fire hazard. Fumigators must therefore be handled with care. The known fumigators further have the serious drawback that the heat of combustion of the combustible material decomposes part of the active ingredient and results in a loss of the active ingredient, consequently affording a lower volatilization efficiency, namely lower effective fugacity rate and reduced efficacy. Measurements in the above method using various insecticides indicate effective fugacity rates lower than 10%. Thus the fumigators heretofore known are not usable with safety and convenience and are unsatisfactory in effectiveness.

An object of this invention is to provide a fumigating method which can be practiced with high safety substantially free of attendant smoke and without involving combustion and an apparatus therefor.

Another object of this invention is to provide a fumigating method and an apparatus therefor capable of effectively quickly giving off the vapor of an active ingredient without entailing a loss of the active ingredient due to the thermal decomposition thereof.

Still another object of this invention is to provide a fumigating method and an apparatus therefor capable of giving off the vapor of an active ingredient uniformly throughout a confined space within a short period of time to produce greatly improved insect-controlling effects.

These and other objects of this invention will become apparent from the following description.

This invention provides a fumigating method comprising heating a mixture of an active ingredient and a blowing agent indirectly with a heating element capable of evolving heat by application of an electric current or a heating element capable of evolving heat by contact with air to thermally decompose the blowing agent without entailing combustion and to volatilize the active ingredient.

Throughout the specification and claims, the term "indirect heating" refers to heating of a mixture of an active ingredient and a blowing agent with the heat given off from a heating element through a heat transfer surface or a partition provided in a container.

We have found that when a mixture of an active ingredient and a blowing agent is heated with the above heating element indirectly to thermally decompose the blowing agent to a gas, the active ingredient can be volatilized with a greatly improved efficiency substantially free of thermal decomposition.

According to the fumigating method of this invention, a large quantity of the vapor of an active ingredient can be emitted and diffused through a confined space without involving combustion or producing smoke which would have a pungent odor and toxicity and without involving any loss of the active ingredient due to the thermal decomposition.

The active ingredients useful in this invention are various and include those heretofore used for insecticidal, fungicidal and incensing purposes. Typical useful examples are as follows.

1. Insecticide (1) 3-allyl-2-methylcyclopenta-2-ene-4-one-1-yl di-cis/-trans-chrysanthemate (available under the trademark "Pynamin", product of SUMITOMO CHEMICAL CO., LTD., Japan, hereinafter referred to as "allethrin A");

(2) 3-allyl-2-methylcyclopenta-2-ene-4-one-1-yl di-cis/-trans-chrysanthemate (available under the trademark "Pynamin-forte", product of SUMITOMO CHEMICAL CO., LTD., Japan, hereinafter referred to as "allethrin B");

(3) d-3-allyl-2-methylcyclopenta-2-ene-4-one-1-yl d-trans-chrysanthemate (available under the trademark "Exlin", product of SUMITOMO CHEMICAL CO., LTD., Japan);

(4) 3-allyl-2-methylcyclopenta-2-ene-4-one-1-yl d-trans-chrysanthemate;

(5) N-(3,4,5,6-tetrahydrophthalimide)-methyl di-cis/-trans-chrysanthemate (available under the trademark "Neopynamin", product of SUMITOMO CHEMICAL CO., LTD., Japan, hereinafter referred to as "phthalthrin");

(6) 5-benzyl-3-furylmethyl d-cis/trans-chrysanthemate (available under the trademark "Chrysron-forte", product of SUMITOMO CHEMICAL CO., LTD., Japan, hereinafter referred to as "resmethrin");

(7) 5-propargyl-3-furylmethyl chrysanthemate;

(8) 3-phenoxybenzyl 2,2-dimethyl-3-(2',2'-dichloro)-vinylcyclopropane-carboxylate (available under the trademark "Eksmin", product of SUMITOMO CHEMICAL CO., LTD., Japan, hereinafter referred to as "permethrin");

(9) 3-phenoxybenzyl d-cis/trans-chrysanthemate (available under the trademark "Sumithrin", product of SUMITOMO CHEMICAL CO., LTD., Japan, hereinafter referred to as "phenothrin");

(10) 0,0-dimethyl 0-(2,2-dichloro) vinylphosphate (hereinafter referred to as "DDVP");

(11) 0-isopropoxyphenyl methylcarbamate;

(12) 0,0-dimethyl 0-(3-methyl-4-nitrophenyl)phosphorothioate;

(13) 0,0-diethyl 0-2-isopropyl-4-methyl-pyrimidyl-(6)-thiophosphate;

(14) 0,0-dimethyl S-(1,2-dicarboethoxyethyl)-dithiophosphate.

Among those insecticides, allethrin A, allethrin B, phthalthrin, resmethrin, permethrin, phenothrin and DDVP are most preferable.

2. Industrial fungicide (1) 2,4,4'-trichloro-2'-hydroxydiphenyl ether (hereinafter referred to as "IF-1");
(2) 2,3,5,6-tetrachloro-4-(methylsulfonyl)-pyridine (hereinafter referred to as "IF-2"); increase in fugacity rate of an active
(3) alkylbenzyl dimethylammonium chloride (to be referred to as "IF-3");
(4) benzyldimethyl {2-[2-(p-1,1,3,3-tetramethyl-butylphenoxy)ethoxy] ethyl} ammonium chloride (to be referred to as "IF-4");
(5) N,N-dimethyl-N-phenyl-N'-(fluorodichloro methylthio) sulfonamide (hereinafter referred to as "IF-5");
(6) 2-(4'-thiazolyl)benzimidazole (hereinafter referred to as "IF-6");
(7) N-(fluorodichloromethylthio)-phthalimide (hereinafter referred to as "IF-7");
(8) 6-acetoxy-2,4-dimethyl-m-dioxine (hereinafter referred to as "IF-8");
(9) salicylic acid;
(10) formalin;
(11) 4-isopropyltropolone;
(12) p-chloro-m-xylenol;
(13) zinc bis (2-pyridinethiol-1-oxide);
(14) sodium-2-pyridinethiol-1-oxide;
(15) diiodo methyl-p-tolyl-sulfone;
(16) p-chlorophenyl-diiodomethyl sulfone;
(17) 2,4-hexadienoic acid;
(18) N-(trichloromethylthio)-4-cyclohexene-1,2-dicarboximide;
(19) 2,4,5,6-tetrachloro isophthalonitrile;
(20) butyl-p-hydroxybenzoate;
(21) 3-trifluoromethyl-4,4'-dichlorocarbanilide;
(22) 2,2'-methylenebis[3,4,6-trichlorophenol];
(23) 2-hydroxyethyl-disulfide;
(24) β-phenoxyethylalcohol;
(25) 1,3-benzenediol;
(26) 1-dodecyl-2-methyl-3-benzyl-imidazolium chloride;
(27) alkyl-diaminoethylene glucine HCl;
(28) polymeric biguanide HCl;
(29) polyoctyl polyamino ethylglycine;
(30) hexahydro-1,3,5-tris-(2-hydroxyethyl)-S-triazine;
(31) polyhexamethylene biguanide HCl;
(32) poly [oxyethylene (dimethylimino) ethylene dichloride];
alkylbetaine type S.A.A.;
(34) bis-(p-chlorophenyldiguanide)-hexanegluconate;
(35) S-bromo-S-nitro-1,3-dioxane;
(36) A mixture of 1,2-benzoisothiazoline-3-one, quarternary ammonium salt and propylene glycol;
(37) alkyldi (aminoethyl)glycine;
(38) alkylisoquinolinium bromide;
(39) 3,4,4'-trichlorocarbanilide;
(40) decamethylene-bis-(4-aminoquinaldinium chloride);
(41) sodium dehydroxyacetate;
(42) 1-oxy-3-methyl-4-isopropylbenzene;
(43) 2-bromo-2-nitropropane-1,3-diol;
(44) sodium p-toluenesulfon choramide;
(45) 1-hexadecylpyridinium chloride;
(46) hexadecyltrimethylammonium bromide.

Among those industrial fungicides, IF-1 to IF-8 are preferable.

3. Antiseptic (1) α-bromo-cinnamaldehyde;
(2) N,N-dimethyl-N-phenyl-N'-(fluorodichloromethylthio)sulfamide.

4. Agricultural fungicide (1) A mixture of bis (dimethylthiocarbamoyl) disulfide, zinc dimethyldithiocarbamate and methylarsenic dimethyldithiocarbamate;
(2) S-benzyl diisopropyl phosphorothioate;
(3) O-ethyl diphenyl phosphorodithioate;
(4) diethyl 4,4'-o-phenylenebis (3-thioallophanate);
(5) dimethyl 4,4'-o-phenylenebis (3-thioallophanate);
(6) N-(trichloromethylthio)-4-cyclohexene-1,2-dicarboximide;
(7) N-(1,1,2,2,-tetrachloroethylthio)-4-cyclohexene-1,2-dicarboximide;
(8) S,S-6-methylquinoxaline-2,3-diyldithiocarbonate;
(9) pentachloronitrobenzene;
(10) methyl 1-(butylcarbamoyl)-2-benzimidazole carbamate;
(11) 2,4-dichloro-6-(o-chloroanilino)-1,3,5-triazine;
(12) 2,3-dicyano-1,4-dithia-1,4-dihydroanthraquinone;
(13) 3-hydroxy-5-methylisoxazole;
(14) streptomycin;
(15) polyoxin;
(16) blasticidin S;
(17) kasugamycin;
(18) validamycin;
(19) 4,5,6,7-tetrachlorophthalide;
(20) N-(dichlorofluoromethylthio)-N',N'-dimethyl-N-phenylsulfamide;
(21) tetrachloroisophthalonitrile;
(22) 2,4-dichloro-6-(o-chloroanilino)-1,3,5-triazine;
(23) ethyl p,p'-dichlorobenzylate;
(24) zinc ethylenebis (dithiocarbamate);
(25) manganese ethylenebis(dithiocarbamate);
(26) complex of zinc and manganese ethylenebis(dithiocarbamate);
(27) dizinc bis(dimethyldithiocarbamate)ethylenebis(dithiocarbamate);
(28) bis(dimethyl-thiocarbamoyl)disulfide;
(29) isomeric reaction mixture of 2,6-dinitro-4-octylphenyl crotonate.

Among the above fungicides, those numbered (21)–(29) are preferable.

5. Plant growth regulant (1) 4-chlorophenoxy acetic acid;
(2) gibberellin;
(3) N-(dimethylamino) succinamide;
(4) α-naphthylacetamide;

6. Herbicide (1) 2,4-D sodium salt;
(2) 3,4-dichloropropionanilide.

7. Repellent (1) 2,3,4,5-bis (Δ$_2$-butylene)-tetrahydrofulfural;
(2) di-n-butyl succinate.

Among the above active ingredients, insecticides are more suited for use in the apparatus of this invention. These active ingredients can be used conjointly with any of synergists, fugacity rate improving agents, deodorants, perfumes, etc. which are usually used. Preferable examples of the synergists are piperonyl butoxide, N-propyl isome, "MGK-264" (product of MCLAUGHLIN GORMLEY KING CO., U.S.A.), "Cynepirin-222" (product of YOSHITOMI PHARMACEUTICAL INDUSTRIES LTD., Japan), "Cynepirin-500" (product of YOSHITOMI PHARMACEUTICAL INDUSTRIES LTD., Japan), "Lethane 384" (product of ROHM AND HAAS COMPANY, U.S.A.), "IBTA" (product of NIPPON FINE CHEMICAL CO., LTD, Japan), "S-421" (product of SANYO CHEMICAL INDUSTRIES, LTD., Japan). Preferable fugacity rate improving agents include phenethylisothiocyanate, dimethylester of himic acid, etc. Preferred deodorants are lauryl methacrylate (LMA), etc. Citral and citronellal are preferably usable as perfumes.

The blowing agent to be used conjointly with the active ingredient and, when desired, with various additives can be any of those generally used and capable of mainly evolving nitrogen gas on thermal decomposition. It is preferable to use compounds which will give off a gas at a temperature of between about 70° C. and about 300° C. The compounds having blowing temperatures far lower than 70° C. tend to decompose by themselves during storage. The compounds with blowing temperatures much higher than 300° C. are likely not to decompose when subjected to heat evolved from the heating element. Accordingly such compounds are not preferable. Examples of typical blowing agents are listed in Table 1 below.

Table 1

| No. | Blowing agent | Abbreviation | Blowing temp. (°C.) |
|---|---|---|---|
| 1. | azodicarbonamide | AC | 200–210 |
| 2. | benzenesulfonylhydraxide | BSH | 100–160 |
| 3. | p-toluenesulfonylhydrazide | TSH | 110 |
| 4. | p,p'-oxybis(benzenesulfonyl-hydrazide) | OSH | 140–160 |
| 5. | dinitrosopentamethylene-tetramine | DPT | 190–205 |
| 6. | N,N'-dinitroso-N,N'-dimethylterephtalamide | DDTP | 90–105 |
| 7. | trihydrazinotriazine | THT | 235–290 |
| 8. | azobisisobutyronitrile | AIBN | 95–105 |
| 9. | 4,4'-azobiscyanovaleric acid | ACVA | 120 |
| 10. | t-butylazoformamide | BAFA | 147–149 |
| 11. | 2,4-bis-(azosulfonyl) toluene | 2,4-TSH | 108–109 |
| 12. | 2,2'-azobisisobutyloamide | AZ-A | 92 |
| 13. | methyl-2,2'-azobisisobutyrate | AZ-B | 85 |
| 14. | 2-(carbamoylazo)isobutyronitrile | CIB | 105 |
| 15. | 1,1'-azobiscyclohexane-1- carbonitrile | ACHC | 115 |

Among the blowing agents listed in Table 1, AC, OSH, DPT, AIBN and ACHC are preferable because they contribute much to the increase in a fugacity rate of an active ingredient. AC in particular remarkably enhances the fugacity rate thereof, produces a gas free of toxicity and pungent odor, and is therefore especially useful.

A blowing agent may be used with additives to reduce the blowing temperature. Preferable examples of the additives are as follows: "Dyhos"(product of NATIONAL LEAD CO., LTD., U.S.A.), "Tribase"(product of NATIONAL LEAD CO., LTD., U.S.A.), "OF-14"(product of ADECA ARGUS CO., LTD., U.S.A.). "OF-15"(product of ADECA ARGUS CO., LTD., U.S.A.), "KV-68A-1"(product of KYODO YAKUHIN CO., LTD., Japan), "Mark-553"(product of ARGUS CHEMI. CO., LTD., U.S.A.), "Sicostab 60"(product of G. Siegle & Co., U.S.A.), "Sicostab 61"(product of G. Siegle & Co., U.S.A.), Cd-stearate, Ca-stearate, Zn-stearate, Zn-octate, ZnO, Sn-maleate, $ZnCO_3$, urea, chrome yellow, carbon black, etc.

According to the invention, the amount of the blowing agent relative to the active ingredient can be determined suitably depending on the use of the resulting composition. Usually it is preferable to use at least about one part by weight of the blowing agent per part by weight of the active ingredient. The effective fugacity rate progressively increases with increasing proportion of the blowing agent, but the use of too great an amount of the blowing agent will not produce significantly improved results. Preferably about one to about 20 parts by weight of the blowing agent is used per part by weight of the active ingredient. The active ingredient and the blowing agent are merely mixed together to prepare a fumigating mixture of this invention but, to ensure efficient production and ease of use, it is desirable to prepare the mixture in the form of powders, granules, pellets, otherwise shaped pieces, paste or the like or to enclose the mixture in a bag of meltable and incombustible resin. The mixture may also be enclosed in an openable bag made of aluminum.

According to this invention, the mixture of an active ingredient and a blowing agent is heated indirectly to thermally decompose the blowing agent without burning the mixture. The heat source is selected from among heating elements capable of evolving heat by application of electric current and those capable of evolving heat by contact with air. Any of heating elements of these types is useful insofar as it is capable of indirectly heating the mixture to such a temperature at which the blowing agent can be decomposed to a gas without burning the mixture. Examples of useful heating elements of the former type are heating wires such as usual nichrome wires, heating carbon elements such as those produced by MATSUSHITA ELECTRIC INDUSTRIAL CO., LTD., Japan, semiconductors such as positive temperatures coefficient thermistors, etc. Examples of useful heating elements of the latter type are compounds which evolve heat on oxidation with the oxygen contained in air. More specific examples include a mixture of sodium sulfide and iron carbide and/or carbon black. Preferably the mixture contains 40 to 60% by weight of sodium sulfide.

According to this invention, the mixture of an active ingredient and a blowing agent is indirectly heated by applying an electric current to the heating element or contacting the same with air depending on the type of the heating element used. To heat the mixture indirectly, the mixture is contained in a suitable container, and the heating element is disposed outside the container. Preferably the mixture and the heating element are accommodated in a container as separated from each other by a partition providing a heat transfer surface. The container is made of heat resistant material such as an iron plate. The mixture and the heating element can be contained in any desired arrangement within the container. The arrangments can be divided into three general types:

(i) Arrangement in which the mixture is positioned above the heating element with a substantially horizontal partition interposed therebetween.

(ii) Arrangement in which the mixture and the heating element are separated from each other by a substantially vertical partition.

(iii) Arrangement in which the mixture and the heating element are separated from each other substantially horizontally and vertically.

In the arrangements (ii) and (iii), it is preferable to arrange the two components concentrically when seen in a plan view, with either one of the two positioned outside the other. In the case of concentric arrangement, the mixture may be accommodated in a plurality of separate compartments. Several kinds of mixtures having varying efficacies can be accommodated in the compartments respectively.

The mixture accommodating compartment has an open upper end which may be kept sealed until the apparatus is put into use. When a material such as polyethylene, polypropylene, polyamide or the like which is meltable but is not burned with the heat evolved from the heating element is used for sealing the compartment, there is no need to remove the seal by hand when using the apparatus, nor any likelihood of hand coming into contact with the mixture, hence convenient and safe.

The meltable seal can be covered with another film or sheet for reinforcing the seal. The covering film or sheet has a number of perforations and may be made from metal such as iron, aluminum or alloy thereof, synthetic resin or paper.

Electric heating elements, when used, are provided preferably in such manner that the heat evolving portion of the element will be in direct contact with part or whole of the partition providing a heat transfer surface, namely of the container wall accommodating the mixture, or will fit to the wall with a heat releasing plate interposed between that portion and the wall. The electric heating element has the advantage of giving a suitable amount of heat with ease at any time desired merely by being connected to an appropriate power supply. Accordingly the electric heating element is usable repeatedly for fumigation in combination with a replaceable cartridge which contains the mixture to be thereby heated and which may be sericeable also as the container for the mixture.

When heating elements which evolve heat on contact with air are used, the element is usable in the form of particles to grains, a sheet or plate or in some other suitable form as contained in an appropriate portion of the apparatus. The heating element must be held out of contact with air, namely in a hermetic state or in an inert gas atmosphere, before the use of the apparatus and must further be maintained in contact with air during use. This can be done easily by enclosing the heating element in a bag of material, such as an aluminum foil, which is impervious to air but readily openable, or by accommodating the heating element in an open compartment of the apparatus and sealing the opening as with an aluminum film. In the latter case, it is preferable to place the heating element into the compartment in a nitrogen gas or like inert gas atmosphere. The heating element thus enclosed can be exposed to air by opening the bag or the seal covering the opening of the compartment.

When the heating element evolves heat, the heat indirectly heats the mixture containing the active ingredient through the partition, thereby decomposing the blowing agent and vigorously volatilizing the active ingredient. According to this invention, the active ingredient can be very effectively volatilized in a large quantity within a short period of time, e.g. a very few minutes or ten-odd minutes, presumably because the blowing agent mixed with the active ingredient gives off a gas on decomposition, forcing the active ingredient to volatilize promptly from the interior of the mixture and because the active agent per se remains free of decompostion due to combustion. The method of this invention, which is capable of very efficiently quickly releasing large quantities of vapors of active ingredients, is useful in controlling noxious insects, such as flies, mosquitoes, fleas, bed bugs, house ticks and cockroaches, which are detrimental to man, as well as plant lice, green house whiteflies, caterpillars and other insects which are harmful to agricultural plants, and is also serviceable for fungicidal and incensing purposes. Additionally the present method is usable for these applications with high safety and great convenience substantially without involving combustion which would produce smoke with toxicity and a pungent odor.

This invention will be described below in greater detail with reference to apparatus suitable for practicing the present method and shown in the accompanying drawings, in which:

FIGS. 1 to 7 are views in vertical section showing the preferred embodiments of apparatus of this invention for practicing the present method.

Figure 2:
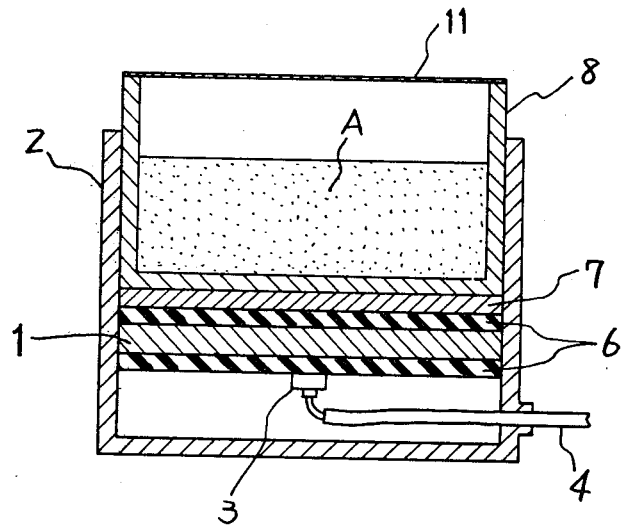
Figure 3:
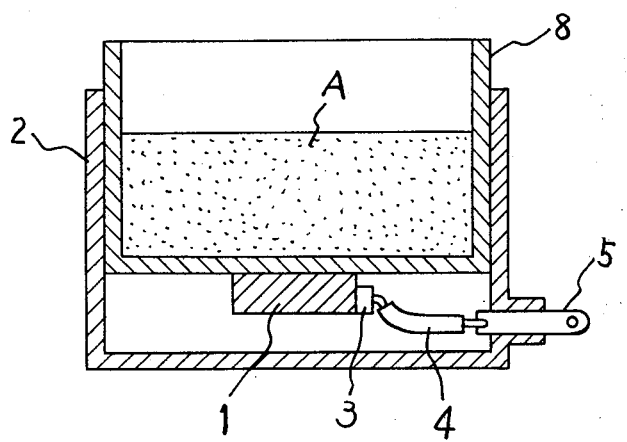

FIGS. 1 to 3 show apparatus each utilizing an electric heating element 1. With the apparatus of FIG. 1, a mixture of an active ingredient and a blowing agent and the heating element are separated from each other vertically and horizontally, whereas FIGS. 2 and 3 each show an apparatus in which the mixture is positioned above and separated from the heating element. The heating elements used in these apparatus are a heating wire (FIG. 1), a heating carbon element (FIG. 2) and a thermistor of positive temperature coefficient (FIG. 3). Each of these heating elements 1 evolves heat upon application of an electric current by being connected to a suitable power supply outside the apparatus. This connection is effected for example via a terminal 3 provided within a container 2 accommodating the heating element 1 and a cord 4 extending outward from the wall of the container 2 as seen in FIG. 1 and FIG. 2 or by way of a plug 5 fixed to the wall of the container 2 as seen in FIG. 3. In view of safety, the heating element 1 can be surrounded by an electrical insulating plate 6. A heat releasing plate 7 can be interposed between a container 8 accommodating the mixture of active ingredient and blowing agent, i.e. mixture A as seen in FIG. 2 and the heating element 1 to achieve an improved thermal efficiency. With the apparatus of FIGS. 1 and 2, the container 8 containing the mixture A is fitted in the upper portion of the container 2 accommodating the heating element 1 and serving as the main body, in which case the mixture A is replaceable as desired along with the container 8. The main body of the apparatus is therefore advantageous in that it is usable repeatedly for the same purpose or for different applications. The apparatus of FIG. 3 includes a container 8 accommodating the mixture A and secured to the upper portion of the container 2 containing the heating element 1, in which case the container 8 is serviceable also as a heat releasing plate. This apparatus is repeatedly usable by replacing the mixture A only. The container 8 for the mixture A may have an open upper end, but the opening is preferably kept sealed until the apparatus is put into use, for example, with a meltable film 11 as seen in FIG. 2. The seal is convenient in that it is spontaneously removable with the heat emitted from the heating element 1. It is desirable that the outer wall of each of the foregoing apparatus, especially the outer wall of the container containing the heating element 1, be of heat insulated construction.

Figure 4:
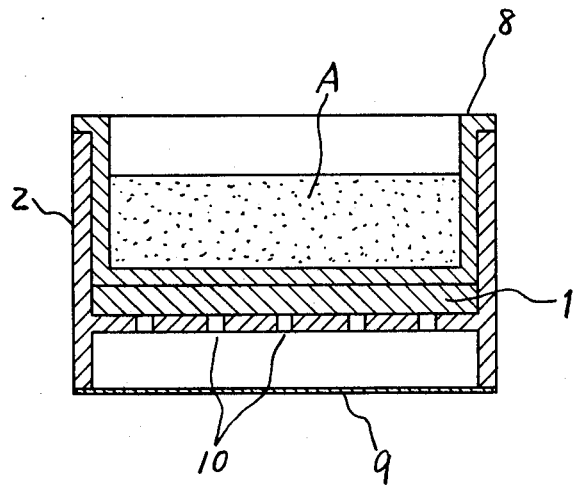
Figure 5:
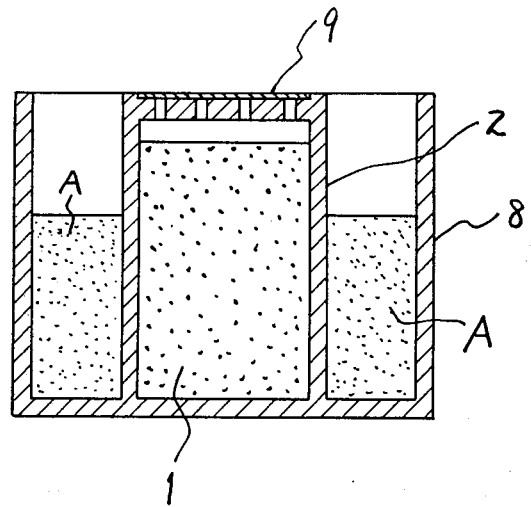

FIGS. 4 to 7 show embodiments each incorporating a heating element which evolves heat on contact with air. The heating element 1 shown in FIG. 4 is in the form of a molded sheet and accommodated in a container 2. A container 8 containing the mixture A is fitted in the upper portion of the container 2 in intimate contact therewith. The heating element 1 shown in FIG. 5 is in the form of grains and placed in a hollow cylindrical inner container 2 which is formed in an outer container 8. The outer container 8 concentric with the inner container 2 contains the mixture A. With the apparatus of FIG. 6 comprising a hollow cylindrical container of the double wall structure, the heating element 1 is shaped in the form of a hollow cylinder and conversely fits around the inner container 8 containing the mixture A. With the apparatus shown in FIG. 7, the heating element 1 is intimately fitted over the side and bottom walls of a container 8 containing a mixture A and is thereby separated from the mixture A.

Figure 6:
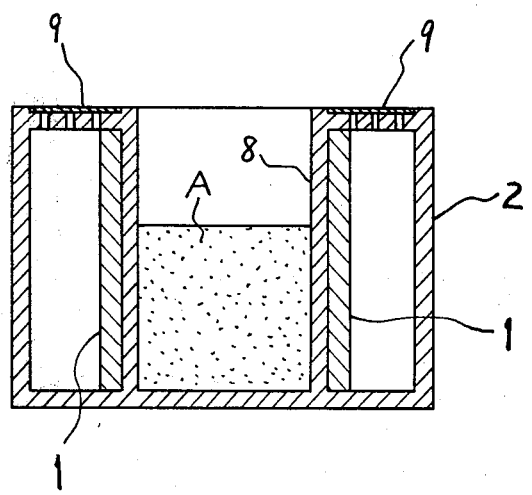
Figure 7:
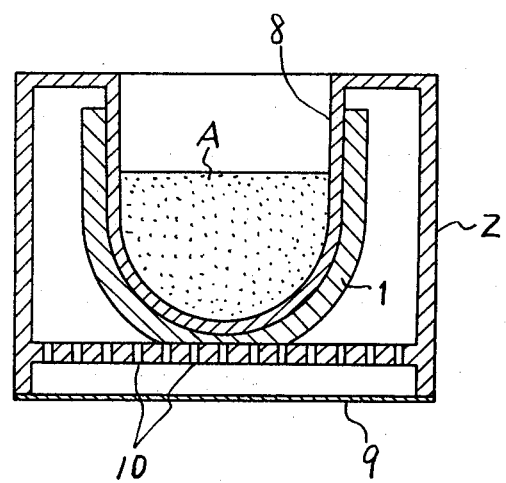

With the apparatus of FIGS. 4 to 7, the container containing the heating element 1 is sealed with a film 9 which is impervious to air and easily openable. When the heating element 1 is disposed in a lower portion or in lower and side portions of the apparatus as shown in FIGS. 4 or 7, the bottom of the container 2 containing the heating element 1 is formed with air apertures 10, and the bottom is covered with the film 9 from outside. In the case of concentric arrangement as shown in FIGS. 5 and 6, the upper end of the container 2 is sealed with the film 9. The heating element 1 evolves heat when the seal portion is opened to expose the element 1 to air, thus indirectly heating the mixture A contained in the container 8 through the partition providing a heat transfer surface, namely the bottom or side wall of the container. The apparatus utilizing the heating elements which evolve heat on contact with air are all very simple in construction and easy to use and require no power supply.

Throughout FIG. 1 to FIG. 7, like numerals indicate like members.

This invention will be described below in greater detail with reference to examples, in which the effective fugacity rates of active ingredients are determined by volatilizing the ingredient within a closed container, passing the air within the container through a solvent which completely dissolves the activde ingredients, such as benzene, acetone, water, chloroform or dichloromethane to cause the solvent to absorb the vaporized ingredient in the air, concentrating the solvent and subjecting the concentrate to gas chromatography. The fugacity rate is expressed in terms of the ratio in percent of the quantity of the active ingredient to the quantity of the ingredient initially admixed with a blowing agent.

EXAMPLE 1

A mixture of an insecticide and a blowing agent as listed in Table 2 is placed into an apparatus of this invention utilizing a heating wire and shown in FIG. 1. An electric current is applied to the wire to indirectly heat the mixture to a temperature of up to 300° C. with the resulting heat, whereby the blowing agent is thermally decomposed to volatilize the insecticide. The effective fugacity rate of the insecticide is determined.

The same procedure as above is repeated except that a mixture of an insecticide, an additive and a blowing agent listed in Table 3 is used.

The results are given in Table 2 and 3.

Table 2

| Specimen No. | Insecticide | (g) | Blowing agent | (g) | Effective fugacity rate (%) |
|---|---|---|---|---|---|
| 1 | allethrin B | 1 | AIBN | 5 | 75.6 |
| 2 | DDVP | 1 | TSH | 10 | 66.5 |
| 3 | " | 1 | 2,4-TSH | 10 | 68.6 |
| 4 | " | 1 | OSH | 10 | 74.6 |
| 5 | allethrin A | 1 | AZ-A | 10 | 63.4 |
| 6 | allethrin A | 1 | AZ-B | 10 | 60.2 |
| 7 | " | 1 | CIB | 10 | 67.1 |
| 8 | " | 1 | ACHC | 10 | 68.7 |
| 9 | allethrin B | 1 | AC | 1 | 60.0 |
| 10 | " | 1 | AC | 3 | 69.3 |
| 11 | " | 1 | AC | 5 | 80.2 |
| 12 | " | 1 | AC | 10 | 79.0 |
| 13 | resmethrin | 1 | AC | 1 | 62.0 |
| 14 | " | 1 | AC | 3 | 74.1 |
| 15 | " | 1 | AC | 5 | 76.5 |
| 16 | " | 0.5 | AC | 2 | 68.8 |
| 17 | " | 0.5 | AC | 4 | 77.0 |
| 18 | " | 0.5 | AC | 5 | 75.5 |
| 19 | " | 0.5 | AC | 10 | 73.2 |
| 20 | " | 0.5 | DPT | 1.5 | 77.3 |
| 21 | phthalthrin | 1 | AC | 5 | 60.2 |
| 22 | phenothrin | 0.5 | AC | 5 | 69.2 |
| 23 | " | 1 | " | 5 | 71.6 |
| 24 | permethrin | 0.5 | " | 5 | 71.6 |
| 25 | " | 1 | " | 5 | 69.4 |
| 26 | DDVP | 0.5 | " | 5 | 79.3 |

Table 3

| Specimen No. | Insecticide | (g) | Additive | (g) | Blowing agent | (g) | Effective fugacity rate (%) |
|---|---|---|---|---|---|---|---|
| 27 | resmethrin | 1 | S-421 | 2 | AC | 3 | 72.8 |
| 28 | " | 1 | piperonyl butoxide | 3 | " | 5 | 78.7 |
| 29 | " | 1 | Lethane 384 | 3 | " | 5 | 78.4 |
| 30 | " | 1 | Cynepirine 222 | 3 | " | 5 | 80.4 |
| 31 | resmethrin | 1 | Cynepirine | 3 | AC | 5 | 79.0 |

Table 3-continued

| Specimen No. | Insecticide | (g) | Additive | (g) | Blowing agent | (g) | Effective fugacity rate (%) |
|---|---|---|---|---|---|---|---|
| 32 | " | 0.5 | 500 citral | 0.1 | " | 2 | 75.5 |
| 33 | " | 0.5 | LMA | 0.1 | " | 1 | 70.0 |
| 34 | " | 0.5 | phenethyl-isothiocyanate | 1 | CELLMIC AN* | 5 | 82.8 |
| 35 | " | 0.5 | dimethyl ester of himic acid | 1 | " | 5 | 82.2 |

* "CELLMIC AN" is a blowing agent manufactured by SANKYO KASEI CO., LTD., JAPAN and containing a mixture of 50% DPT and 50% urea as an additive.

COMPARATIVE EXAMPLE 1

The same procedure as in Example 1 is repeated without using any blowing agent. Table 4 shows the results.

Table 4

| Specimen No. | Insecticide | (g) | Effective fugacity rate (%) |
|---|---|---|---|
| 36 | resmethrin | 1 | 0.6 |
| 37 | allethrin B | 1 | 2.9 |
| 38 | phenothrin | 1 | 1.3 |
| 39 | permethrin | 1 | 0.9 |

COMPARATIVE EXAMPLE 2

The mixtures listed in Table 5 each composed of an insecticide and a combustible material as in known fumigants, were burned for fumigation. Table 5 also shows the effectively fugacity rates achieved.

Table 5

| Specimen No. | Insecticide | (g) | Combustible material | (g) | Effective fugacity rate (%) |
|---|---|---|---|---|---|
| 40 | resmethrin | 0.5 | nitro-cellulose (30%) | 30 | 6.3 |
| 41 | allethrin B | 0.5 | " | 30 | 1.7 |
| 42 | phthalthrin | 0.5 | " | 30 | 7.2 |
| 43 | phenothrin | 0.5 | " | 30 | 8.1 |
| 44 | permethrin | 0.5 | " | 30 | 8.6 |

Tables 2 to 5 show that the method of this invention using the present apparatus results in remarkably improved effective fugacity rate.

EXAMPLE 2

A mixture of an insecticide and a blowing agent as listed in Table 6 is placed into the container 8 of an apparatus of this invention as shown in FIG. 4. A heating element (20g) in the form of a mixture of 4 parts by weight of sodium sulfide and 6 parts by weight of iron carbide is brought into contact with air by removing the seal 9 to heat the container to about 300° C. with the resulting heat from outside, whereby the blowing agent is thermally decomposed to volatilize the insecticide. The effective fugacity rate achieved by the insecticide is determined. Table 6 shows the results.

Table 6

| Specimen No. | Insecticide | (g) | Blowing agent | (g) | Effective fugacity rate (%) |
|---|---|---|---|---|---|
| 45 | allethrin B | 1 | AIBN | 5 | 69.3 |

Table 6-continued

| Specimen No. | Insecticide | (g) | Blowing agent | (g) | Effective fugacity rate (%) |
|---|---|---|---|---|---|
| 46 | DDVP | 1 | TSH | 10 | 60.5 |
| 47 | DDVP | 1 | 2,4-TSH | 10 | 61.8 |
| 48 | allethrin B | 1 | AC | 3 | 73.5 |
| 49 | allethrin A | 1 | AZ-A | 10 | 63.5 |
| 50 | " | 1 | AZ-B | 10 | 61.0 |
| 51 | allethrin B | 1 | AC | 5 | 80.5 |
| 52 | allethrin A | 1 | ACHC | 10 | 66.0 |
| 53 | resmethrin | 1 | AZ-B | 10 | 60.3 |
| 54 | " | 1 | AC | 3 | 70.2 |
| 55 | " | 1 | AC | 5 | 75.6 |
| 56 | " | 0.5 | DPT | 1.5 | 78.6 |
| 57 | phthalthrin | 0.5 | AZ-A | 10 | 60.4 |

EXAMPLE 3

A mixture of a fungicide and a blowing agent as listed in Table 7 is placed into the hollow cylindrical container 8 of an apparatus as shown in FIG. 1. The compartment is externally heated with the heating wire 1 to a temperature of up to 300° C. to thermally decompose the blowing agent and to thereby volatilize the fungicide. The effective fugacity rate achieved by the fungicide is determined. Table 7 also shows the results.

Table 7

| Specimen No. | Fungicide | (g) | Blowing agent | (g) | Effective fugacity rate (%) |
|---|---|---|---|---|---|
| 58 | IF-2 | 0.5 | AIBN | 5 | 61.4 |
| 59 | " | 0.5 | AC | 5 | 71.3 |
| 60 | " | 0.5 | AZ-A | 10 | 60.7 |
| 61 | IF-8 | 0.5 | AZ-B | 10 | 61.3 |
| 62 | " | 0.5 | AIBN | 5 | 57.8 |
| 63 | " | 0.5 | ACHC | 5 | 62.3 |
| 64 | IF-7 | 0.5 | AZ-B | 5 | 61.0 |
| 65 | " | 0.5 | AC | 5 | 65.0 |
| 66 | " | 0.5 | CIB | 5 | 56.9 |
| 67 | IF-6 | 0.5 | DPT | 1.5 | 72.1 |
| 68 | IF-3 | 0.5 | AZ-A | 3 | 81.5 |
| 69 | IF-2 | 0.5 | AIBN | 10 | 71.3 |
| 70 | IF-1 | 0.5 | " | 5 | 75.3 |
| 71 | IF-4 | 0.5 | " | 5 | 55.4 |
| 72 | IF-7 | 1 | AZ-A / AZ-B | 2 / 2 | 57.9 |

COMPARATIVE EXAMPLE 3

The procedure of Example 3 is repeated using a fungicide listed in Table 8 but without using any blowing agent. Table 8 also shows the results.

Table 8

| Specimen No. | Fungicide | (g) | Effective fugacity rate (%) |
| --- | --- | --- | --- |
| 73 | IF-5 | 1 | 7.0 |
| 74 | IF-8 | 1 | 9.0 |
| 75 | IF-7 | 1 | 2.0 |
| 76 | IF-2 | 1 | 11.0 |

Tables 7 and 8 reveal that the use of blowing agent conjointly with a fungicide enables the fungicide to volatilize with an efficiency which is ten-odd times to several tens of times as high as the efficiency achieved by the same quantity of the fungicide when it is heated alone at the same temperature. Active ingredients placed in the present apparatus are tested for the quantity of smoke evolved, toxicity and insecticidal effect by being volatilized by the method of Example 1.

Quantity of smoke (turbidity)

An apparatus of this invention accommodating the same mixture as Specimen No. 18 is used in a chamber 90cm×90cm×90cm to volatilize the active ingredient. For comparison, a fumigating composition composed of 30g of a combustible material and 1.5g of DDVP is burned in the same chamber as above.

The chamber is transparent in the upper part and is lit up with a fluorescent light (20w) provided in the upper center of the chamber. A marking plate is horizontally disposed in vertically movable manner in the chamber. The marking plate is a white disc made of plastic with a diameter of 35mm. On the disc are drawn four black lines 0.5mm in width such that two pairs of lines are intersected at a right angle in the center of the disc, two lines of each pair being spaced in parallel with a distance of 0.1mm. The above disc is vertically moved to measure the longest distance (h) between the top of the chamber and the disc at which the four lines on the disc are clearly seen with unaided eyes. In this way, turbidity within the chamber is calculated by the following equation:

Turbidity (%) = $h$(cm)/90(cm) × 100

The same procedure is repeated five times for each specimen, giving the following average data.

| | Distance(cm) | Turbidity(%) |
| --- | --- | --- |
| Present invention: | 68 | 75.6 |
| Comparison: | 16 | 17.8 |

The results indicate that the quantity of smoke emitted from the apparatus of this invention is substantially negligible.

Toxicity

A toxicity test is conducted under the following conditions.

(1) Apparatus
A: Apparatus accommodating Specimen No. 16 of this invention.
B: Apparatus accommodating Specimen No. 18 of this invention.
(2) Device
Chambers, 1m×1m×1m (i.e. 1m$^3$).
(3) Animals
Five-week-old mice JCL: ICR (4) Method
Five male mice or five female mice are placed into a chamber, ther interior of the chamber is fumigated with one or two apparatus and the animals are left confined in the chamber for 2 hours. The animals are thereafter placed into an ordinary cage and given a diet and water.
(5) Results
Tables 9 and 10 show the results.

Table 9

| | | Number of deaths | | | | | |
| --- | --- | --- | --- | --- | --- | --- | --- |
| | | Immediately after the fumigation | | One day after the fumigation | | Two days after the fumigation | |
| Test No. | Apparatus | M. | F. | M. | F. | M. | F. |
| 1 | A (one) | 0 | 0 | 0 | 0 | 0 | 0 |
| 2 | B (one) | 0 | 0 | 0 | 0 | 0 | 0 |
| 3 | B (two) | 0 | 0 | 0 | 0 | 0 | 0 |

Specimens No.16 and No.18 used in the toxicity test cause no death, and the test animals are alive 10 days after the fumigation. As shown in Table 9, high safety is ensured when using the present apparatus in a chamber having a concentration of the volatilized active ingredient over 30 times the concentration thereof at which a satisfactory insecticidal effect is achieved.

Table 10 shows the changes in the body weight of the animals surviving the test.

Table 10

| | | Body weight of the animals (average in g) | | | | | | |
| --- | --- | --- | --- | --- | --- | --- | --- | --- |
| Test No. | Animal's sex | before test | 1 day after | 2 days after | 4 days after | 6 days after | 8 days after | 10 days after |
| 1 | M. | 26.7 | 27.8 | 26.7 | 30.1 | 29.9 | 30.1 | 31.9 |
| | F. | 22.8 | 23.0 | 22.2 | 23.6 | 24.0 | 23.0 | 23.8 |
| 2 | M. | 25.4 | 26.8 | 26.2 | 29.0 | 27.6 | 29.0 | 30.4 |
| | F. | 22.9 | 23.1 | 22.3 | 24.5 | 24.3 | 24.9 | 25.1 |
| 3 | M. | 26.1 | 29.1 | 28.9 | 31,7 | 32.1 | 32.5 | 34.7 |
| | F. | 22.7 | 22.7 | 22.1 | 23.5 | 24.1 | 24.3 | 25.1 |

Table 10 reveals that the specimens of the invention show substantially no harmful effect on the increasing rate of body weight of the tested animals and that they are substantially free from toxicity. The amounts of food taken by the animals is slightly reduced only on the first day after the test but thereafter no change is observed.

Insecticidal effect

1. Specimens of this invention are tested for insecticidal effect under the following conditions.
(1) Test insects
Adults of german cockroaches.
(2) Method
A laboratory dish (24 cm in inside diameter and 6.5cm in height) containing 25 test insects is placed in each corner of a closed room, 3m×4m×3m (height), i.e. 36m$^3$, and the interior of the room is fumigated with a specimen placed in the center of the room. Knockdown is determined at a specified time interval after the initiation of fumigation. Two hours after the fumigation, the test insects are transferred to a rearing chamber, and mortality (%) is determined in 24 hours and 48 hours. In the rearing chamber, the insects are given a diet and water. Table 11 shows the results.

Table 11

| Specimens No. | | 11 | 22 | 24 | 18 |
|---|---|---|---|---|---|
| Knockdown (%) | 30 min. | 53 | 51 | 45 | 53 |
| | 60 min. | 98 | 94 | 83 | 100 |
| | 90 min. | 100 | 97 | 95 | 100 |
| | 120 min. | 100 | 100 | 100 | 100 |
| Mortality (%) | 24 hr. | 76 | 65 | 96 | 80 |
| | 48 hr. | 100 | 100 | 100 | 100 |

Table 11 shows that the use of the present apparatus in a closed room leads to effective extermination of noxious vermin.

2. Specimen No.18 of this invention is further tested for insecticidal effect in a simulated living room.

(1) Test insects

Adults of german cockroaches and adults of american cockroaches.

(2) Method

A 76-cm-high desk having four drawers in layers is placed in one corner of a room, 3m in width, 4m in length and 3m in height, i.e. 36m$^3$. A wood box (45 cm × 41 cm × 37 cm) is placed in another corner of the room as spaced apart by 2 cm from the wall, with its opening opposed to the wall. A closed box (measuring 30cm × 30cm and having 8 holes of 7mm in diameter in its top side) is placed on a 150-cm-high shelf in the center of one of the longitudinal walls of the room, the box being positioned close to the wall.

Laboratory dishes (24 cm in inside diameter and 6.5cm in height) each containing 20 adults of german cockroaches and 10 adults of american cockroaches are placed in various locations within the room. The interior of the room is fumigated with a specimen placed in the center of the room, and the insects are left confined in the room for one hour. The insects are thereafter transferred into a rearing case and given a diet and water. Mortality (%) is determined 24 hours and 48 hours after the start of the experiment.

The dishes are placed in the following locations:

P$_1$: In the open box.

P$_2$: In the closed box.

P$_3$: In the uppermost closed drawer of the desk.

P$_4$: In the second highest drawer of the desk as withdrawn by 1 cm.

P$_5$: In the lowermost drawer of the desk as withdrawn by 2 cm.

(3) Specimen

Specimen No. 18.

(4) Results

Table 12 shows the results achieved with the german cockroaches, and Table 13 those with american cockroaches.

Table 12

| | | Place | | | | |
|---|---|---|---|---|---|---|
| | | P$_1$ | P$_2$ | P$_3$ | P$_4$ | P$_5$ |
| Mortality(%) | 24 hr. | 49 | 34 | 48 | 39 | 35 |
| | 48 hr. | 100 | 95 | 100 | 100 | 100 |

Table 13

| | | Place | | | | |
|---|---|---|---|---|---|---|
| | | P$_1$ | P$_2$ | P$_3$ | P$_4$ | P$_5$ |
| Mortality(%) | 24 hr. | 9 | 19 | 28 | 10 | 19 |
| | 48 hr. | 88 | 60 | 100 | 79 | 100 |

Tables 12 and 13 show that the method of this invention achieves outstanding insect controlling effect at various locations.

What we claim is:

1. A fumigating method comprising heating a mixture of an active ingredient and a blowing agent indirectly with a heating element capable of evolving heat by application of an electric current or a heating element capable of evolving heat by contact with air to thermally decompose the blowing agent without entailing combustion and to volatilize the active ingredient, said blowing agent being decomposable at a temperature of between about 70° C. and about 300° C. to give off mainly nitrogen gas and contacting an object, material or area to be treated with the so-generated fumigant.

2. A method as defined in claim 1 wherein the active ingredient is an insecticide.

3. A method as defined in claim 1 wherein the active ingredient is a fungicide.

4. A method as defined in claim 1 wherein the mixture is indirectly heated with a heating element capable of evolving heat by application of an electric current.

5. A method as defined in claim 4 wherein the heating element capable of evolving heat by application of an electric current is a heating wire, a heating carbon element or a thermistor of positive temperature coefficient.

6. A method as defined in claim 1 wherein the mixture is indirectly heated with a heating element capable of evolving heat by contact with air.

7. A method as defined in claim 6 wherein the heating element capable of evolving heat by contact with air is a mixture of sodium sulfide and at least one of iron carbide and carbon black.

8. A method as defined in claim 1 wherein said blowing agent is at least one species selected from the group consisting of azodicarbonamide, benzenesulfonylhydrazide, p-toluenesulfonylhydrazide, p,p'-oxybis(benzenesulfonylhydrazide), dinitrosopentamethylene tetramine, N,N'-dinitroso-N,N'-dimethylterephthalamide, trihydrazinotriazine, azobisisobutyronitrile, 4,4'-azobiscyanovaleric acid, t-butylazoformamide, 2,4-bis-(azosulfonyl) toluene, 2,2'-azobisisobutyloamide, methyl-2,2'-azobisisobutyrate, 2-(carbamoylazo) isobutyronitrile, and 1,1'-azobiscyclohexane-1-carbonitrile.

9. A method as defined in claim 8 wherein the blowing agent is at least one species selected from the group consisting of azodicarbonamide, p,p'-oxybis(benzenesulfonylhydrazide), dinitrosopentamethylenetetramine, azobisisobutyronitrile and 1,1'-azobiscyclohexane-1-carbonitrile.

10. A method as defined in claim 9 wherein said blowing agent is azodicarbonamide.

11. A fumigating apparatus for practicing the method as defined in claim 1 comprising accommodated therein a mixture of an active ingredient and a blowing agent, and a heating element capable of evolving heat by application of an electric current, the mixture and the heating element being separated from each other by a partition interposed therebetween and providing a heat transfer surface, said blowing agent being decomposable at a temperature of between about 70° C. and about 300° C. to give off mainly nitrogen gas.

12. An apparatus as defined in claim 11 wherein the mixture and the heating element are separated from each other horizontally and vertically by the partition.

13. An apparatus as defined in claim 11 wherein a container containing the mixture is fitted in the upper portion of a container containing the heating element.

14. A fumigating apparatus for practicing the method as defined in claim 1 comprising accommodated therein a mixture of an active ingredient and a blowing agent, and a heating element capable of evolving heat by contact with air, the mixture and the heating element being separated from each other by a partition interposed therebetween and providing a heat transfer surface, said blowing agent being decomposable at a temperature of between about 70° C. and about 300° C. to give off mainly nitrogen gas.

15. An apparatus as defined in claim 14 wherein the mixture and the heating element are separated from each other horizontally and vertically by the partition.

16. An apparatus as defined in claim 14 wherein the heating element is contained in a container having an opening sealed with an openable film of air-impervious material, the heating element being held out of contact with air.

* * * * *